US00PP34118P2

(12) United States Plant Patent
Gräb

(10) Patent No.: US PP34,118 P2
(45) Date of Patent: Apr. 12, 2022

(54) CHERRY TREE NAMED 'KSG 24 A'

(50) Latin Name: *Prunus avium*
Varietal Denomination: KSG 24 A

(71) Applicant: Lizenzen für Früchte und Pflanzen GmbH, Bassenheim (DE)

(72) Inventor: Hilmar Gräb, Bassenheim (DE)

(73) Assignee: Lizenzen für Früchte und Pflanzen GmbH, Bassenheim (DE)

( * ) Notice: Subject to any disclaimer, the term of this patent is extended or adjusted under 35 U.S.C. 154(b) by 0 days.

(21) Appl. No.: 17/300,411

(22) Filed: Jun. 18, 2021

(51) Int. Cl.
*A01H 5/08* (2018.01)
*A01H 6/74* (2018.01)

(52) U.S. Cl.
USPC ..... Plt./181

(58) Field of Classification Search
USPC ..... Plt./181
See application file for complete search history.

*Primary Examiner* — Susan McCormick Ewoldt
(74) *Attorney, Agent, or Firm* — Michelle Bos Legal LLC

(57) ABSTRACT

'KSG 24 A' is a self-fruitful sweet cherry tree distinguished by its late harvest maturity and consistent yield of large, attractive fruit with excellent flavor and texture.

5 Drawing Sheets

Latin name: *Prunus avium.*
Variety denomination: 'KSG 24 A'.

BACKGROUND AND SUMMARY OF THE VARIETY

The new sweet cherry tree 'KSG 24 A' originated in the applicant's breeding program, where it was selected from seedlings obtained from the open pollination of female parent 'Sumtare' (not patented) by an unknown male parent at Kettig, Germany in 2004. Initial asexual propagation by grafting onto Gisela® 5 rootstock ('GI 148/2', U.S. Plant Pat. No. 9,622) was carried out at Kettig in 2006. 'KSG 24 A' was initially selected for its late harvest maturity and consistent yield of large, attractive fruit with excellent flavor and texture.

The broad kidney-shaped fruit of 'KSG 24 A' is distinguishable from the heart-shaped fruit of parent 'Sumtare'. The varieties are further distinguished by the later bloom time of 'KSG 24 A' as compared to the early bloom time of 'Sumtare'.

'KSG 24 A' is similar to sweet cherry variety 'Sumpaca' (not patented) in that both varieties are self-fertile and are similarly productive. 'KSG 24 A' can be distinguished from 'Sumpaca' by its later bloom time and harvest maturity.

'KSG 24 A' is distinguished from related varieties 'KSG 03 A' (co-pending application Ser. No. 17/300,401) and 'KSG 16 A' (co-pending application Ser. No. 17/300,410) as shown in Table 1 below.

TABLE 1

Comparison of 'KSG 24 A' to related varieties

| | 'KSG 24 A' | 'KSG 16 A' | 'KSG 03 A' |
|---|---|---|---|
| Harvest maturity | Late | Mid-season to late | Very late |
| Tree vigor | Weak | Medium-strong | Medium-strong |
| Fruit color | Dark red (greyed-purple 187A) | Black (black 203B) | Dark red (greyed-purple 187A) |

TABLE 1-continued

Comparison of 'KSG 24 A' to related varieties

| | 'KSG 24 A' | 'KSG 16 A' | 'KSG 03 A' |
|---|---|---|---|
| Fruit shape | Broad kidney-shaped | Heart-shaped | Oblong heart-shaped |
| Fruit size | 15 g | 13 g | 12 g |
| Bloom time | Early mid-season | Very late | Early to mid-season |

The 'KSG 24 A' cherry tree has been found to exhibit its distinctive characteristics and remain stable through successive asexually propagated generations.

BRIEF DESCRIPTION OF THE PHOTOGRAPHS

The accompanying photographs, taken in 2016 at Kettig, Germany, show 10-year-old trees grown on Gisela® 5 rootstock.

Figure 1:
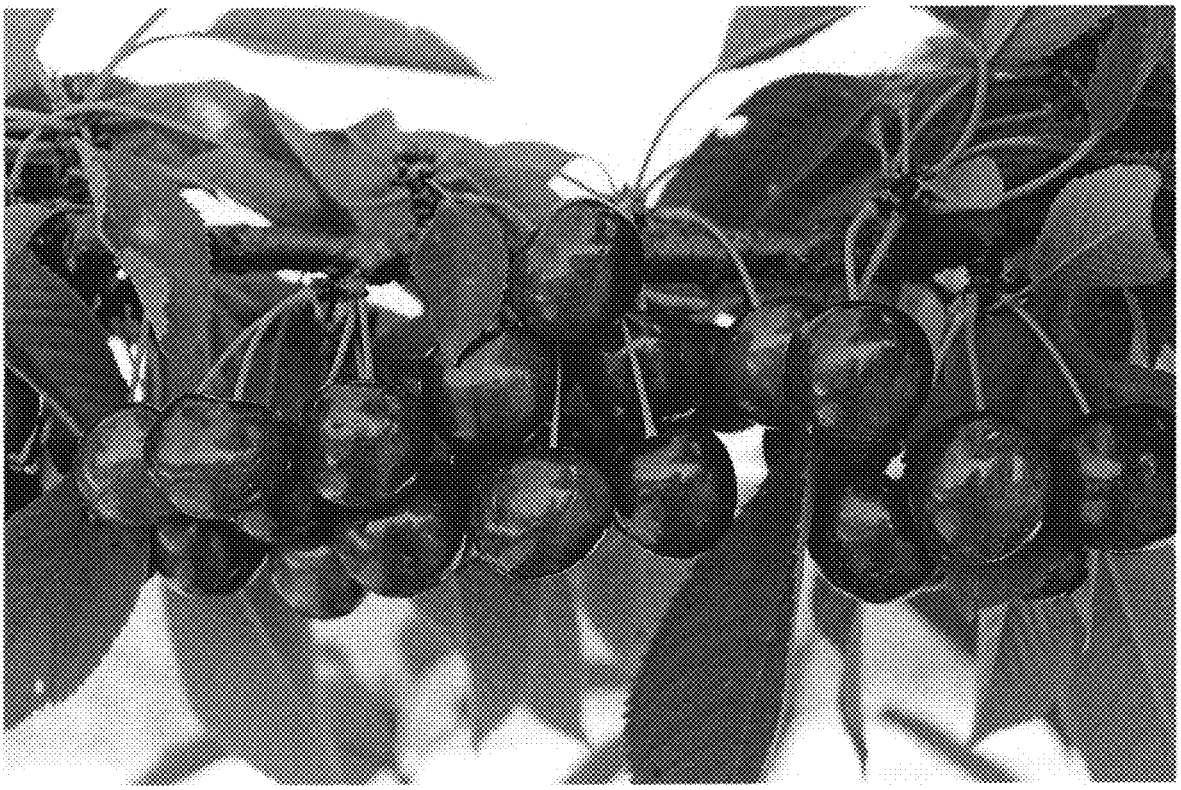
Figure 2:
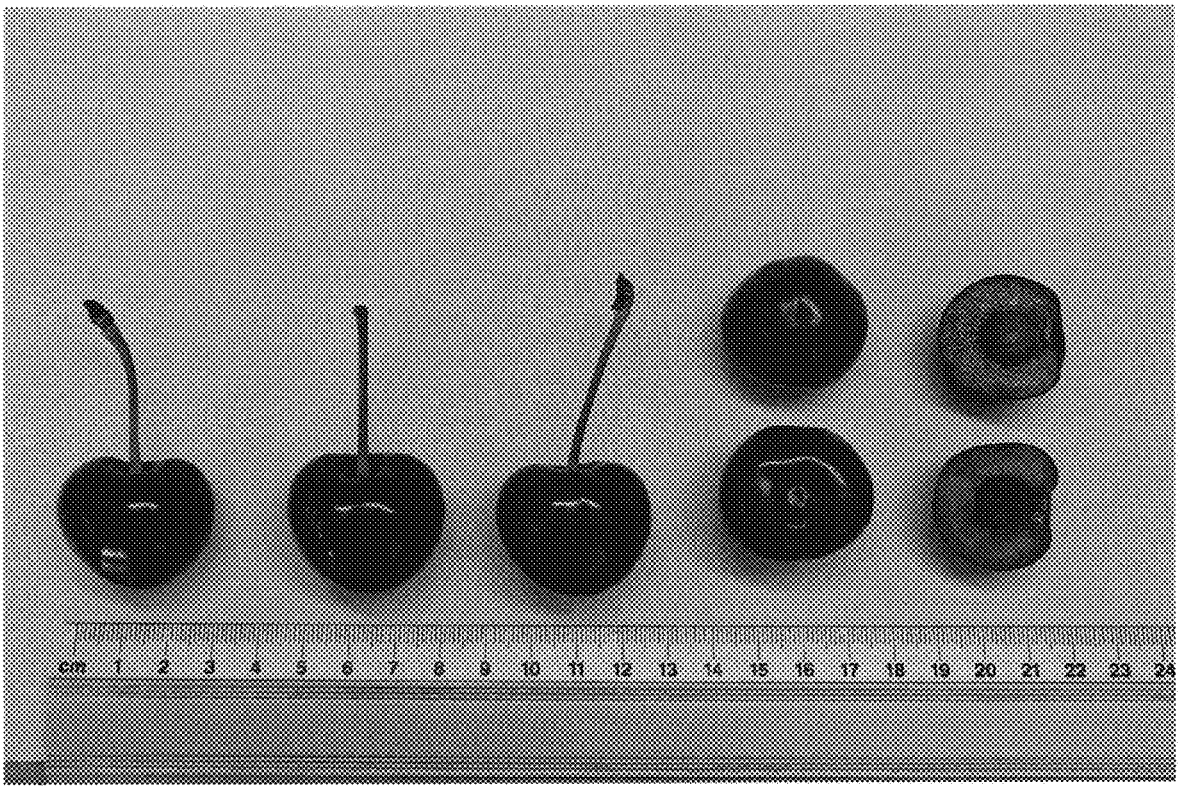
Figure 3:
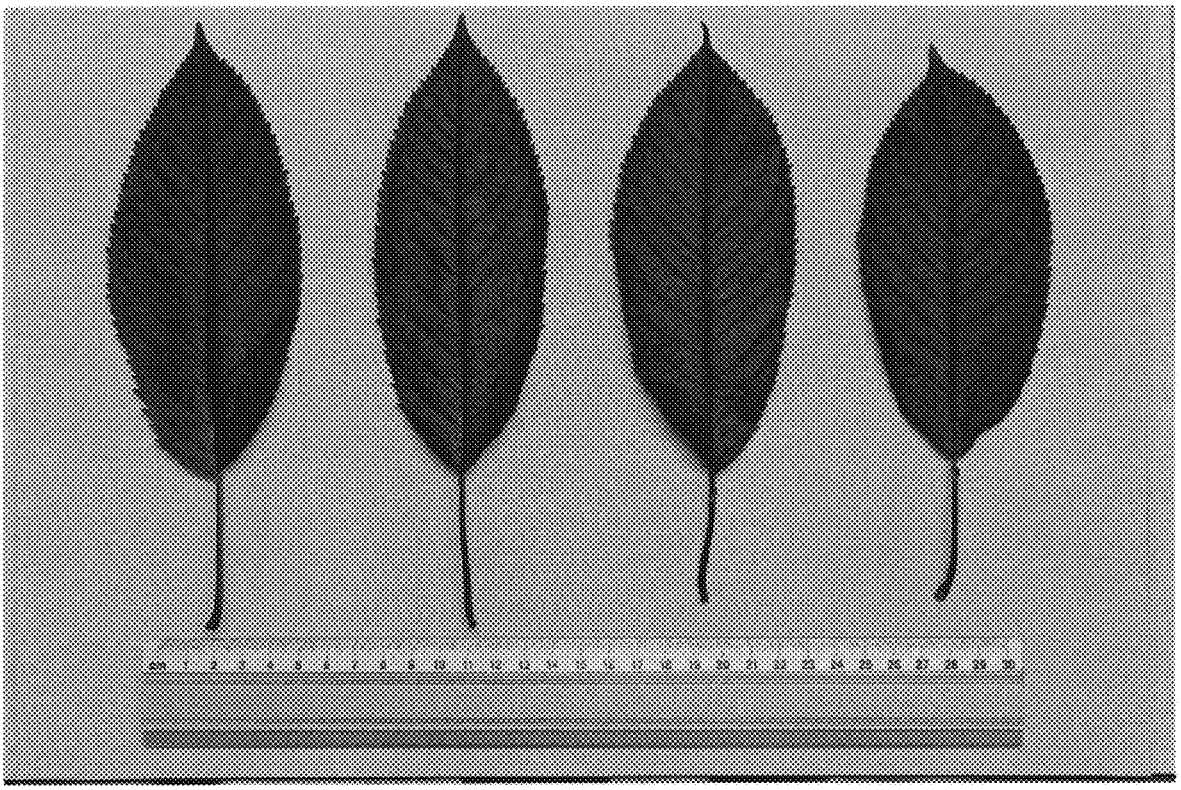
Figure 4:
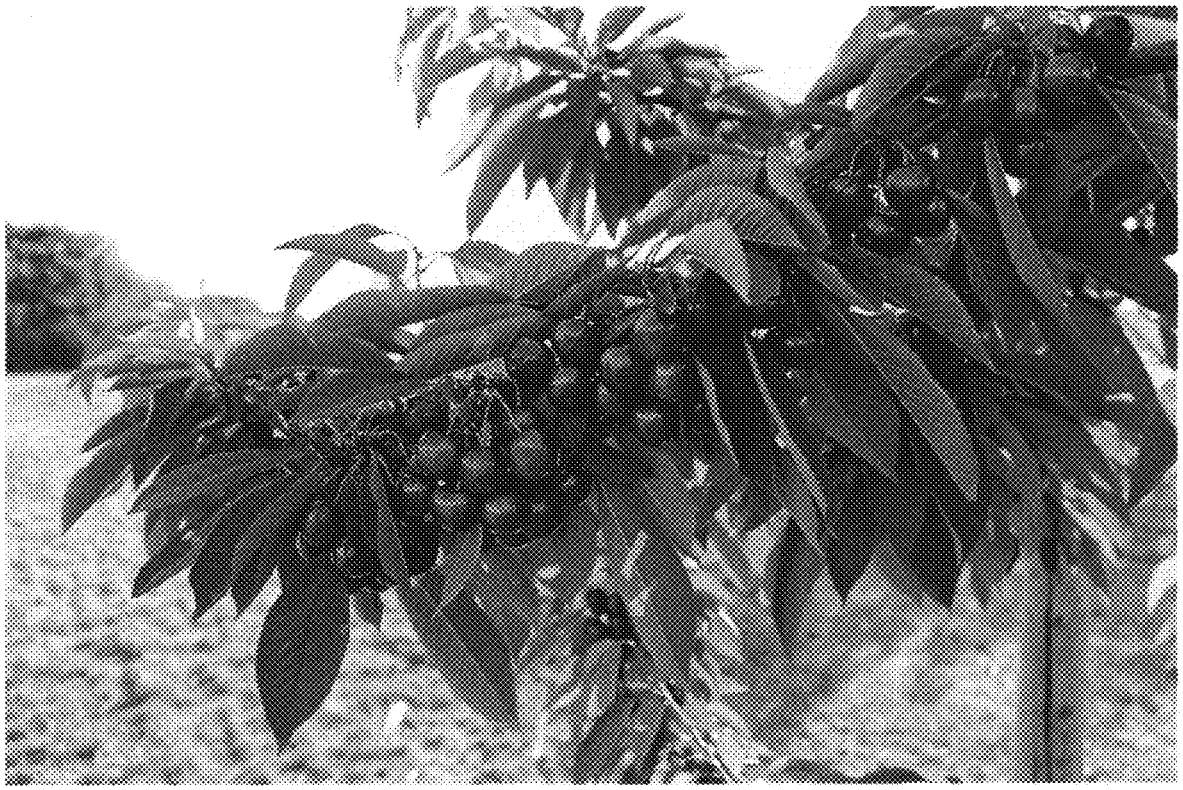
Figure 5:
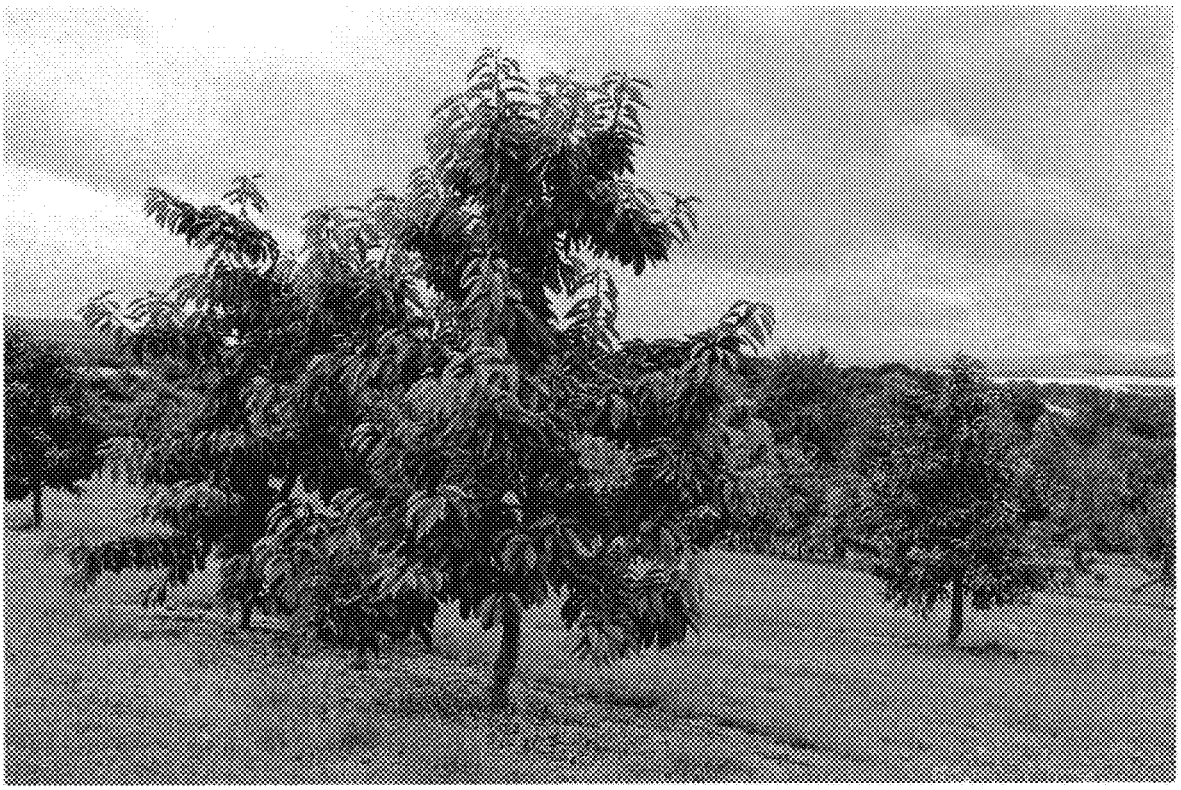

FIG. 1 shows the fruit and leaves of 'KSG 24 A';
FIG. 2 shows the fruit of 'KSG 24 A';
FIG. 3 shows the leaves of 'KSG 24 A';
FIG. 4 shows a branch, fruit and leaves of 'KSG 24 A'; and
FIG. 5 shows a tree of 'KSG 24 A'.

The colors shown in these photographs may vary with lighting conditions. Color characteristics of the claimed variety should therefore be determined with reference to the observations described herein, rather than from the photographs alone.

DETAILED BOTANICAL DESCRIPTION

The following detailed botanical description is based on observations recorded in 2016 at Kettig, Germany, of 10-year-old trees grown on Gisela® 5 rootstock. The characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average. Color descriptions are made with reference to The R.H.S. Colour Chart (Royal Horticultural Society, 6th ed.).

Tree:
- *Vigor*.—Weak.
- *Habit, shape*.—Upright to spreading.
- *Density*.—Moderate.
- *Height*.—2.8 m.
- *Spread*.—2.3 m.
- *Trunk diameter*.—7 cm at 80 cm above the graft.
- *Trunk texture*.—Smooth.
- *Bark color*.—Greyed-purple 183A.
- *Lenticel length*.—2.5 mm to 7 mm.
- *Lenticel width*.—1.3 mm to 2.4 mm.
- *Lenticel color*.—Greyed-orange 167A.
- *Lenticel density*.—Low to medium.
- *Production*.—Precocious, moderate to high yield; 15 kg per tree (Gisela® 5 rootstock, central leader system).

One-year-old shoots:
- *Diameter*.—6.0 mm.
- *Surface texture*.—Smooth.
- *Color*.—Grey-brown N199B.
- *Crotch angle*.—Upright.
- *Buds*.—Alternate arrangement, short internode length, round, slightly raised.
- *Lenticel length*.—1 mm to 2 mm.
- *Lenticel width*.—1 mm to 2 mm.
- *Lenticel shape*.—Mostly round.
- *Lenticel density*.—Low.
- *Lenticel color*.—Greyed-orange 164A.

Flower buds:
- *Pedicel length*.—15.3 mm.
- *Pedicel diameter*.—1.5 mm.
- *Pedicel color*.—Yellow-green 144A.
- *Bud length*.—12 mm.
- *Bud diameter*.—5.5 mm.
- *Bud shape*.—Ovate with slightly rounded to pointed tip.
- *Bud color*.—Green 143A.

Flowers:
- *Bloom timing*.—Early mid-season, similar to 'Sumele' (not patented).
- *Bloom duration*.—Long, 10 to 12 days.
- *Pollination requirement*.—Self-fertile.
- *Number of flowers per raceme*.—25 to 30, mostly 3 to 5 per unit, very high density.
- *Fragrance*.—Sweet.
- *Flower diameter*.—36 mm.
- *Petals*.—5 per flower, overlapping.
- *Petal length*.—16 mm.
- *Petal width*.—14 mm.
- *Petal shape*.—Round.
- *Appearance*.—White, clear shell-shaped venation at base, moderately transparent.
- *Margin*.—Smooth.
- *Texture*.—Veined.
- *Petal color when opening*.—Both surfaces white NN155D with red 39D at tip.
- *Petal color when fully open*.—Both surfaces white NN155D.

Sepals:
- *Quantity*.—5 per flower.
- *Shape*.—Elongated oval.
- *Margin*.—Entire, sides of base serrulate.
- *Texture*.—Smooth.
- *Length*.—8 mm.
- *Width*.—4 mm.
- *Color*.—Both surfaces green 143B.

Stamens:
- *Quantity per flower*.—35 to 40.
- *Filament length*.—10 mm.

Anthers:
- *Shape*.—Rounded, divided in two.
- *Diameter*.—0.8 mm.
- *Color*.—Greyed-orange N163A, N163B.

Pistils:
- *Quantity*.—1 per flower.
- *Length*.—16 mm including stigma and ovary.

Style:
- *Length*.—13 mm.
- *Color*.—Green 142C.

Stigma:
- *Shape*.—Clearly divided in two, T-shaped.
- *Color*.—Yellow 1C.

Leaves:
- *Length*.—11.5 cm to 16.0 cm, average 13.5 cm.
- *Width*.—4.5 cm to 7 cm, average 5.9 cm.
- *Form*.—Elliptic with acuminate tip and acute base.
- *Texture*.—Smooth, moderately glossy.
- *Thickness*.—Medium.
- *Margin*.—Dentate to serrate.
- *Arrangement*.—Alternate.
- *Pubescence of upper surface*.—None.
- *Pubescence of lower surface*.—Minimal.
- *Color of young leaf upper surface*.—Green 143A.
- *Color or young leaf lower surface*.—Green 143C.
- *Color of mature leaf upper surface*.—Green 139A.
- *Color of mature leaf lower surface*.—Green 147B.
- *Petiole shape*.—Rounded.
- *Petiole length*.—3.9 cm.
- *Petiole diameter*.—2.5 mm.
- *Petiole color*.—Yellow-green 145A with anthocyanin coloration.
- *Venation texture*.—Smooth on leaf upper surface; prominent on lower surface.
- *Vein color*.—Green 139A on upper surface; Yellow-green 146C on lower surface.

Fruit:
- *Maturity when described*.—Mature.
- *Harvest timing*.—Late.
- *Diameter*.—31 mm to 36 mm, average 33 mm.
- *Length*.—26 mm to 30 mm, average 28 mm.
- *Weight*.—Average 15 g.
- *Shape*.—Broad kidney-shaped.
- *Skin thickness*.—Thin to medium.
- *Skin texture*.—Smooth.
- *Tendency to crack*.—Low to medium tendency at stalk cavity.
- *Skin color*.—Greyed-purple 187A.
- *Flavor*.—Sweet, aromatic.
- *Soluble solids*.—18° Brix at full maturity.
- *Flesh color*.—Red 47A.
- *Juice color*.—Greyed-purple 184B.
- *Texture*.—Melting, full-bodied, very juicy.

Seed:

*Height.*—11.8 mm to 13.7 mm, average 12.7 mm.
*Width.*—10 mm.
*Circumference.*—31 mm.
*Form.*—Round.
*Color.*—Orange-white 159C.

Stem:

*Length.*—35 mm to 45 mm, average 40.5 mm.
*Diameter.*—1.6 mm to 2.2 mm, average 1.8 mm.
*Color.*—Green 143C.

Market use: Fresh consumption.
Eating quality: Very good.
Storability: Very good.
Winter hardiness: Tree and buds cold-hardy in area tested.

The invention claimed is:

1. A new and distinct cherry tree named 'KSG 24 A', substantially as illustrated and described.

* * * * *